(12) United States Patent
Chen et al.

(10) Patent No.: US 6,552,024 B1
(45) Date of Patent: Apr. 22, 2003

(54) COMPOSITIONS AND METHODS FOR MUCOSAL DELIVERY

(75) Inventors: Li-Lan H. Chen, Edison; William R. Pfister, Robbinsville, both of NJ (US); Donald W. Renn, Glen Cove, ME (US); Thitiwan Buranachokpaisan, Milltown, NJ (US); James Osborne, Princeton Junction, NJ (US); Hock Seng Tan, Old Bridge, NJ (US); Li Tao, Edison, NJ (US)

(73) Assignee: Lavipharm Laboratories Inc., Hightstown, NJ (US)

( * ) Notice: Subject to any disclaimer, the term of this patent is extended or adjusted under 35 U.S.C. 154(b) by 0 days.

(21) Appl. No.: 09/434,878

(22) Filed: Nov. 5, 1999

Related U.S. Application Data (60) Provisional application No. 60/116,823, filed on Jan. 21, 1999.

(51) Int. Cl.[7] .......................... A61K 31/495; A61K 9/00; A61K 9/14; A61K 9/70; A61K 31/24; A61K 31/44; A61K 31/50; A61K 31/505; A61K 31/56

(52) U.S. Cl. .................. 514/252.16; 424/400; 424/443; 424/444; 424/484; 424/485; 424/486; 424/487; 424/488; 514/182; 514/258; 514/289; 514/343; 514/534

(58) Field of Search ................................ 424/400, 443, 424/444, 484, 485, 486, 487, 488; 514/182, 252.16, 258, 289, 343, 534

(56) References Cited

U.S. PATENT DOCUMENTS

| | | | |
|---|---|---|---|
| 4,029,757 A | 6/1977 | Mlodozeniec et al. | 424/452 |
| 4,029,758 A | 6/1977 | Mlodozeniec et al. | 424/452 |
| 4,031,200 A | 6/1977 | Reif | 424/459 |
| 4,059,686 A | 11/1977 | Tanaka et al. | 424/19 |
| 4,128,445 A | 12/1978 | Sturzenegger et al. | 156/64 |
| 4,136,145 A | 1/1979 | Fuchs et al. | 264/164 |
| 4,136,162 A | 1/1979 | Fuchs et al. | 424/443 |
| 4,414,198 A | 11/1983 | Michaelson | 424/44 |
| 4,572,832 A | 2/1986 | Kigasawa et al. | 424/19 |
| 4,680,323 A | 7/1987 | Lowey | 524/43 |
| 4,683,256 A | 7/1987 | Porter et al. | 524/285 |
| 4,721,709 A | 1/1988 | Seth et al. | 514/211 |
| 4,777,046 A | 10/1988 | Iwakura et al. | 424/435 |
| 4,876,092 A | 10/1989 | Mizobuchi et al. | 424/435 |
| 4,900,552 A | 2/1990 | Sanvordeker et al. | 424/422 |
| 4,935,243 A | 6/1990 | Borkan et al. | 424/441 |
| 4,946,684 A | 8/1990 | Blank et al. | 424/441 |
| 4,950,664 A | 8/1990 | Goldberg | 514/219 |
| 4,983,385 A | * 1/1991 | Hasegawa et al. | 514/772.4 |
| 5,004,601 A | 4/1991 | Snipes | 424/78 |
| 5,013,557 A | 5/1991 | Tai | 424/493 |
| 5,047,244 A | 9/1991 | Sanvordeker et al. | 424/435 |
| 5,073,374 A | 12/1991 | McCarty | 424/435 |
| 5,077,053 A | 12/1991 | Kuncewitch et al. | 424/441 |
| 5,112,616 A | 5/1992 | McCarty | 424/435 |
| 5,135,752 A | 8/1992 | Snipes | 424/435 |
| 5,166,202 A | 11/1992 | Schweizer | 514/220 |
| 5,166,233 A | 11/1992 | Kuroya et al. | 524/37 |
| 5,198,436 A | 3/1993 | Ellinwood, Jr. et al. | 514/221 |

(List continued on next page.)

FOREIGN PATENT DOCUMENTS

| | | |
|---|---|---|
| CA | 1263312 | 11/1989 |
| DE | 196 46 392 A1 | 5/1998 |
| EP | 0 084 705 A2 | 8/1983 |
| EP | 0 124 027 A1 | 11/1984 |
| EP | 0 200 508 A2 | 10/1986 |
| EP | 0 124 027 B1 | 6/1990 |
| EP | 0 371 466 A1 | 6/1990 |
| EP | 0 404 490 A1 | 12/1990 |
| EP | 0 553 777 A2 | 8/1993 |
| EP | 0 586 034 A2 | 3/1994 |
| EP | 0 627 218 A1 | 12/1994 |
| EP | 0 711 547 A1 | 5/1996 |
| WO | WO 93/23017 | 11/1993 |
| WO | WO 95/01782 | 1/1995 |
| WO | WO 95/20377 | 8/1995 |
| WO | WO 95/34293 | 12/1995 |

OTHER PUBLICATIONS

JP 04363332 A Patent Abstract, Dec. 16, 1992, Toru et al.
JP 08291051 A Patent Abstract, Nov. 5, 1996, Tatara et al.
JP 09216816 A Patent Abstract, Aug. 19, 1997, Nakamichi et al.
JP 09309821 Patent Abstract, Dec. 2, 1997, Nakamichi et al.
JP 09309822 Patent Abstract, Dec. 2, 1997, Nakamichi et al.
JP 10053518 Patent Abstract, Feb. 24, 1998, Kayane et al.
JP 62081432 A Patent Abstract, Apr. 14, 1987, Morohoshi et al.
JP 62135417 A Patent Abstract, Jun. 18, 1987, Tatara et al.
JP 63310818 A Patent Abstract, Dec. 19, 1998, Tatara et al.
PCT/JP92/01631—Translation, *Intrabuccally Disintegrating Preparation and Production Thereof*

(List continued on next page.)

*Primary Examiner*—Jose' G. Dees
*Assistant Examiner*—Frank Choi
(74) *Attorney, Agent, or Firm*—Dechert; Thomas S. Deibert (57) ABSTRACT

Mucosal surface-coat-forming film dosage units containing a water-soluble hydrocolloid, an effective dose of an active agent and a mucosal adhesion enhancer; wherein the active agent is encapsulated within a polymer which is chemically or physically distinct from the hydocolloid; wherein the mucosal adhesion enhancer is a starch graft copolymer; wherein the film exhibits a dry tack value of less than 3.5 g, a wet tack of greater than 35 g, a gelation temperature that is greater than 70° C. for a 2% polymer solution, a dry film thickness of less than 20 mil, a water content of 0.5 to 10%, a tensile strength greater than 1500 psi, a modulus in the range of 35,000 to 300,000 psi, a % elongation of less than 20%, a tear probagation resistance of 0.001 to 1 N, and a dissolution time in the range of 1 to 600 seconds upon application to an oral mucosal surface.

51 Claims, 6 Drawing Sheets

U.S. PATENT DOCUMENTS

| | | |
|---|---|---|
| 5,223,264 A | 6/1993 | Wehling et al. ............. 424/466 |
| 5,229,130 A | 7/1993 | Sharma et al. ............. 424/449 |
| 5,229,164 A | 7/1993 | Pins et al. ................. 264/510 |
| 5,244,668 A | 9/1993 | Snipes ........................ 424/435 |
| 5,288,497 A | 2/1994 | Stanley et al. ............. 424/440 |
| 5,346,701 A | 9/1994 | Heiber et al. .............. 424/435 |
| 5,378,473 A | 1/1995 | Sharma et al. ............. 424/449 |
| 5,413,792 A | 5/1995 | Ninomiya et al. .......... 424/434 |
| 5,430,029 A | 7/1995 | Biella et al. ................ 514/220 |
| 5,466,464 A | 11/1995 | Masaki et al. ............. 424/434 |
| 5,472,704 A | 12/1995 | Santus et al. .............. 424/435 |
| 5,474,783 A | 12/1995 | Miranda et al. ............ 424/448 |
| 5,501,861 A | 3/1996 | Makino et al. ............. 424/464 |
| 5,529,789 A | 6/1996 | Lo .............................. 424/473 |
| 5,558,880 A | 9/1996 | Gole et al. .................. 424/484 |
| 5,567,439 A | 10/1996 | Myers et al. ............... 424/486 |
| 5,569,466 A | 10/1996 | Tanner et al. .............. 424/452 |
| 5,576,014 A | 11/1996 | Mizumoto et al. ......... 424/435 |
| 5,595,761 A | 1/1997 | Allen, Jr. et al. ........... 424/484 |
| 5,629,003 A | 5/1997 | Horstmann et al. ........ 424/401 |
| 5,635,210 A | 6/1997 | Allen, Jr. et al. ........... 424/465 |
| 5,648,093 A | 7/1997 | Gole et al. .................. 424/484 |
| 5,650,192 A | 7/1997 | Britton et al. ............. 427/2.19 |
| 5,662,920 A | 9/1997 | Santus ........................ 424/435 |
| 5,700,478 A | 12/1997 | Biegajski et al. ........... 424/434 |
| 5,716,928 A | 2/1998 | Benet et al. .................. 514/11 |
| 5,720,974 A | 2/1998 | Makino et al. ............. 424/464 |
| 5,731,339 A | 3/1998 | Lowrey ....................... 514/400 |
| 5,770,606 A | 6/1998 | El-Rashidy et al. ........ 514/284 |
| 5,807,576 A | 9/1998 | Allen, Jr. et al. ........... 424/465 |
| 5,948,430 A | 9/1999 | Zerbe et al. ................ 424/435 |

OTHER PUBLICATIONS

Alderman, D., A Review of Cellulose Ethers in Hydrophilic Matrices for Oral Controlled–Release Dosage Forms, *Int. J. Pharm. tech & Prod. Mfr.*, 5 (3) 1–9, 1984.

Ahuja, A. et al., Mucoadhesive Drug Delivery Systems, *Drug Development and Industrial Pharmacy*, 23 (5), 489–515, 1997.

Brewster, D. et al., The systemic bioavailability of buprenorphine by various routes of administration, *J. Pharm. Pharmacol.*, 33, 500–506, 1981.

Christie, J. et al., Dose–Titration, Multicenter Study of Oral Transmucosal Fentanyl Citrate for the Treatment of Breakthrough Pain in Cancer Patients Using Transdermal Fentanyl for Persistent Pain, *Journal of Clinical Oncology*, vol. 16, No. 10, 3238–3256, Oct., 1998.

Feely, et al., The influence of polymeric excipients on drug release from hydoxypropylmethylcellulose matrices, *International Journal of Pharmaceutics*, 44, 131–139, 1988.

Gandhi et al., Oral cavity as a site for bioadhesive drug delivery, *Advanced Drug Delivery Reviews*, 13, 43–74, 1994.

Harris et al, Drug Delivery via the Mucous Membranes of the Oral Cavity, *Journal of Pharmaceutical Sciences*, vol. 81, No. 1, 1–10, Jan., 1992.

Ponchel, G., Formulation of oral mucosal drug delivery systems for the systemic delivery of bioactive materials, *Advanced Drug Delivery Reviews*, 13, 75–87, 1994.

Rathbone, M. et al., The oral cavity as a site for systemic drug delivery, *Advanced Drug Delivery Reviews*, 13, 1–22, 1994.

Russell, W. et al., Pharmacokinetics of a New Sublingual Formulation of Temazepam, *European Journal of Clinical Pharmacology*, 35, 437–439, 1988.

Sasaki et al., Kinetics of Buccal Absorption of Propafenone Single Oral Loading Dose in Healthy Humans, *Gen. Pharmac.*, vol. 331, No. 4, 589–591, 1998.

Streisand, et al., Oral Transmucosal Etomidate in Volunteers, *Anesthesiology*, 88, 899–95, 1998.

Yamanouchi, In Pursuit of New Drug Delivery Technologies, Annual Report 1996, http://www.yamanouchi.com/eg/ar96/ar06.html.

Zhang, J. et al., Buccal Absorption of Etomidate from a Solid Formulation in Dogs, *Anesth. Analg.*, 86, 1116–22, 1998.

* cited by examiner

COMPOSITIONS AND METHODS FOR MUCOSAL DELIVERY

RELATED APPLICATIONS

This application gains priority from Provisional Application No. 60/116,823 filed Jan. 21, 1999.

TECHNICAL DESCRIPTION

The present invention is directed to a device and method for administering agents in a dissolving film configuration.

BACKGROUND TO THE INVENTION

Many pharmaceutical dosage forms are administrated orally in the form of solid shaped articles such as tablets, pills, caplets and capsules that retain their shape under moderate pressure. Generally these dosage forms are designed to be swallowed whole or chewed to deliver the medication with adequate amounts of liquid. Some patients, particularly pediatric and geriatric patients, have difficulty swallowing or chewing solid dosage forms. Certain patients such as children or animals resist taking medication, and may try to hide a solid pill in order to spit it out later. In addition, many pediatric and geriatric patients are unwilling to take a solid dosage form because the active agent is difficult to swallow or is retained in the pharynx or gullet even when liquids are consumed with the dosage unit. Furthermore, the availability of liquids at the time of administering medications may be limited for certain patients and may be restricted for certain diseases and/or treatments. Chewable tablets provide some advantages over the conventional tablets. However, they are not suitable for children wearing braces and the taste of the medication may be unpleasant and difficult to mask in a chewable tablet. At the same time, water may be still required for the administration of chewable tablets.

In addition, the standard oral dosage forms, such as tablets, pills, caplets, and capsules, are designed for short residence time in the mouth. Absorption of the agent from these dosage forms occurs in the gastrointestinal (GI) tract, after the agent has separated from the dosage form and dissolved in the gastric fluids. For some active agents, it is desirable to achieve absorption through the oral mucosal tissues in order to accelerate onset of the therapeutic effect.

Many active agents are poorly absorbed, even after they are dispersed in the stomach, because of low solubility or slow dissolution rate in the gastric fluids. Tablets may be formulated so as to be quick dissolving. These tablets are commonly placed on the tongue and disintegrate rapidly in the oral cavity. However, these dosage units are not fixed to a mucosal surface and may move around in the mouth. Consequently, they do not overcome a risk associated with choking or gagging that occurs with subjects having limited control of their swallowing reflexes. However, once placed in the mouth, these tablets dissolve rapidly in the saliva to provide a liquid formulation which is then swallowed. Quick dissolving tablets may be formed from a particulate support matrix containing the therapeutic agent, where the particulate support matrix is a protein (U.S. Pat. Nos. 5,807,576, 5,635,210, 5,595,761). Alternatively, the tablet may be formed from a laminate with several layers and an outer coating (JP 100535518). Tablets have also been manufactured from shearform matrices which are substantially amorphous sugar formed when crystalline sugar is subjected to heat and shear (WO 95/07194; WO 95/35293). Other methods of forming quick dissolving tablets include wet granulation methods (EP 0627 218) and dry granulation methods (EP 0124027A1) and by freeze-drying techniques (EP 0084705A2). Generally, quick dissolving tablets are formed using complex multi-step manufacturing processes. In addition, these tablets may have poor mechanical strength, are fragile and friable and have insufficient holding capacity for active ingredients (U.S. Pat. No. 5,720,974) and may be difficult to store and handle.

Therapeutic compounds are sometimes provided as powders or granules which may be difficult to swallow and cause unpleasant sensations in the mouth. Furthermore, many quick dissolving tablets contain particulates (>25 microns) which leave a "gritty" and unpleasant taste in the mouth. In the elderly, powders may cause choking and discomfort associated with trapping of granules in dentures. Powders and granules are generally packaged in a sealed pouch which requires tearing before use. This causes problems for geriatric patients and those suffering from arthritis in the fingers as well as for children. Consequently, problems of spillage of the contents arise in this group of patients. Furthermore, these oral preparations should be taken with water which for certain patients are inconvenient and may cause reduced patient compliance.

Liquid, syrups or suspensions are an alternative to solid dosage forms and are considered desirable for pediatric and geriatric patients who have problems in swallowing tablets. However, these dosage forms are often difficult to measure accurately and administer easily. Liquid formulations deteriorate rapidly upon exposure to heat or atmosphere and consequently have a relatively short shelf life. Furthermore, liquid formulations require a relatively large volume and are bulky to store.

In addition to solid and liquid dosage forms, rapidly dissolving buccal/oral delivery systems have been developed. These systems are commonly freeze dried preparations which are more expensive to manufacture as compared to tablets (U.S. Pat. No. 5,648,093). Furthermore, freeze dried preparations are brittle and fragile when handled and must be kept in dry conditions to avoid disintegration. The instability of freeze-dried preparations has been reduced somewhat by the addition of mannitol (U.S. Pat. No. 4,946,684). WO 9820862 reports a film that is formed according to a method that does not utilize freeze drying and avoids problems described in the art such as rigidity of the films, delayed softening and poor solubility in the mouth (U.S. Pat. No. 4,876,092; EP 0200508; EPO 381194; CA-PS 1-26331; DE 2449865.5; DE 3630603; EP 0452446 and EP 0219762). However, the film described in WO 9820862 relies on the use of at least two different non-ionic surfactants to achieve immediate wettability.

It is desirable that a dosage unit should provide a non-invasive, effective and economic means to deliver an active agent to the target site. Where the target site is the plasma, additional issues arise concerning the rate of delivery of the active agent to that site as measured by bioavailability. For many types of active agent, fast onset of the therapeutic effect is desirable. Traditional oral dosages, such as tablets, are limited in onset time by the rate of absorption in the gastro-intestinal tract. Formulations have been developed which, when applied in the mouth, lead to faster onset that the traditional oral dosages because they target the oral mucosa. These formulations include dosage units containing 75%–90% polyethylene glycol that melt at body temperature, in the mouth.(U.S. Pat. No. 5,004,601 and 5,135,752) Other formulations include liquid forms, lozenges or tablets that are administered sublingually or by a sweetened matrix on a stick. (U.S. Pat. No. 5,770,606, Streisand et al. and Zhang et al., Christie et al., Sasaki et al.). Whereas the above references address the delivery route, they do not address the problems of bioavailability that arise from poor solubility or low dissolution rate.

A delivery device that addresses the above limitations would represent a desirable improvement on existing delivery systems.

SUMMARY OF THE INVENTION

A novel dosage unit and its method of manufacture and use is provided. In an embodiment, the dosage unit includes a water-soluble hydrocolloid, mucosal surface-coat-forming film, such film including an effective dose of an active agent. In an embodiment of the invention, the hydrocolloid includes a polymer selected from the group consisting of a natural, semi-natural and synthetic biopolymer being exemplified by a polysaccharide and a polypeptide. In addition to the hydrocolloid, the film may further include one or more of an emulsifier, a plasticizer, a taste modifying agent, a water soluble inert filler, a preservative, a buffering agent, a coloring agent, a permeation enhancer, and a stabilizer. The film may further include an active agent selected from the group consisting of a therapeutic agent, a dietary supplement and a hygiene aid. Embodiments of the invention utilize effective amounts of sildenafil citrate, nicotine, hydromorphone, oxybutynine or estradiol as active agents in the dosage unit. The active agent may be encapsulated within a second polymer having dissolution properties that are different from those of the hydrocolloid. More than one active agent may be included in the film. In an embodiment of the invention, the emulsifier may have a concentration of 0.1–10% w. The water inert filler may include a concentration range of 0.5–50% and the preservative may include a concentration range of 0.01–10%. A mucosal adhesion enhancer such as starch graft copolymer may be included in the dosage unit.

In embodiments of the invention, the dosage unit may further include any of the following features: a dry film thickness in the range of 1–20 mil, more particularly less than 10 mils, a dry tack value of less than 3.5 g, more particular less than 2 g, a wet tack value of greater than 35 g, a tensile strength greater than 1500 psi, a modulus in the range of 35,000–300,000 psi, a tear propagation resistance in the range 0.0001N–1N, a disintegration time in a range from 1–300 seconds, a dissolution time in a range from 10–600 seconds, and a percentage elongation less than 20%.

In embodiments of the invention, methods are provided for making a dosage unit, that include in one embodiment, dissolving a hydrocolloid in a solvent so as to form a substantially homogeneous preparation; adding to the hydrocolloid preparation, an active agent and at least one reagent selected from the group consisting of an emulsifier, a plasticizer, a taste modifier, a water soluble inert filler, a coloring agent, a preservative, a permeation enhancer, a stabilizer and a buffering agent to form a coatable mixture; and forming a mucosal surface-coat forming film from the mixture for packaging as a dosage unit. The method may further include the step of coating the mixture onto a backing film. In a further embodiment, the reagents including: a hydrocolloid, an active agent, and at least one reagent selected from the group consisting of an emulsifier, a plasticizer, a taste modifier, a water soluble inert filler, a coloring agent, a preservative, a permeation enhancer, a stabilizer, and a buffering agent, may be combined in any order in a vessel having a heating source and a mechanical mixing device, the combined ingredients being mixed during and after the addition of the ingredients to the vessel, an effective amount of heat being applied for melting a substantial portion of the mixture. The mixture may then be formed into a film in a dry extrusion process.

In an embodiment of the invention, a method is provided for administering an active agent to a subject, that includes obtaining a water-soluble hydrocolloid, mucosal surface-coat-forming film, such film including an effective dose of an active agent; and placing the film on a mucosal surface coat forming film in the subject; so as to release the active agent.

In a further embodiment of the invention, a dosage unit is provided that includes a water soluble hydrocolloid and an effective dose of sildenafil citrate in a mucosal-surface contacting film. More particularly, an effective dose of sildenafil citrate is formed into a solid dispersion with xylitol for treating erectile dysfunction. The sildenafil/xylitol dispersion may be mixed with at least one reagent selected from the group consisting of an emulsifier, a plasticizer, a taste modifier, a coloring agent, a preservative, a permeation enhancer, a stabilizer and a buffering agent. The solid dispersion of sildenafil and xylitol may arise at a ratio of 9 parts sildenafil to one part xylitol. According to embodiments of the invention directed to a dosage unit and method of making a dosage unit suitable for erectile dysfunction, the water solubility of sildenafil in the solid dispersion is at least 20 mg/ml, more particularly about 50 mg/ml. More particularly, the film may be capable of completely dissolution at the oral mucosal surface within 10–600 seconds.

DETAILED DESCRIPTION OF INVENTION

Delivery of active agents in solid form via the mouth causes problems to patients who may choke on the dosage unit. This effect is caused at least in part by the mobility of the dosage unit within the mouth. We have developed a new class of dosage units which are not mobile in the mouth because on contact with the moist mucosal surface, the film becomes a coating that adheres to the mucosal surface and then disintegrates and dissolves over a time frame controlled in the design of the dosage. The dosage unit, in an embodiment of the invention, is in the form of a flexible, non-tacky, dry conveniently packaged film. Once removed from the package and placed on a mucosal surface, the mucosal surface-coat-forming film hydrates substantially immediately to form a coating on the moist surface of the mucous membrane and then disintegrates and dissolves to release the active agent from the film.

The dosage unit may release the active agent over a period of time that is determined by a number of different factors. These factors include the dimensions of the film, the concentration of the active agent, the solubility of the agent at the mucosal surface and how the agent is dispersed throughout the film. The thickness of the film is a factor in determining the rate of dissolution. A thick film will dissolve more slowly than an otherwise similar thin film. A thick film may be desirable for its holding capacity for active agents that are required in high dosages. Although the surface area of a film can be adjusted up to about 5 square centimeters, increased thickness may also be desirable for purposes of achieving effective active agent dosages. The active agent can form a solid dispersion with a water soluble inert filler for purposes of increasing the solubility of the agent when released from the film thereby enhancing bioavailability of the active agent. This is exemplified here by sildenafil which is incorporated in a film with a water soluble inert filler, for example, xylitol, which has been found here to enhance the bioavailability of this agent. Solubilizing agents that are well known in the art may be included in the film. The extent of uptake of the active agent from the dosage unit at the mucosal surface can be controlled by the dissolution rate of the film. A dissolving film will release the active agent and this in turn will cause the active agent to be swallowed and taken up in the GI tract. In contrast, slow release of the active agent at the mucosal surface will give rise to increased uptake by the mucosal surface. A further parameter governing the release of an active agent at the mucosal surface is the manner in which the agent is dispersed in the film. For example, the agent may be dispersed as colloidal particles or microencapsulated within the film or alternatively may be mixed throughout the film as a reagent during casting.

The dosage unit of the invention may be used as a vehicle for delivering a wide range of active agents. For example, the active agent may be a small molecule, a protein, a nucleic acid including antisense molecules or other biological or synthetic molecules.

The term "mucosal surface-coat-forming" as applied to a film as used in this description and in the following claims unless specified otherwise , means a film that coats the mucosal surface on contact, and may not thereafter be manually recovered or moved from the contact site; and subsequently disintegrates and dissolves so as to release the active agent. It should be noted that for purposes of the description of the invention and the claims, "mucosal surface" refers to any moist surface of the body. This includes the surfaces identified in FIG. 1. It further includes a wound surface where lymph fluid bathes the tissue surface.

Figure 1:
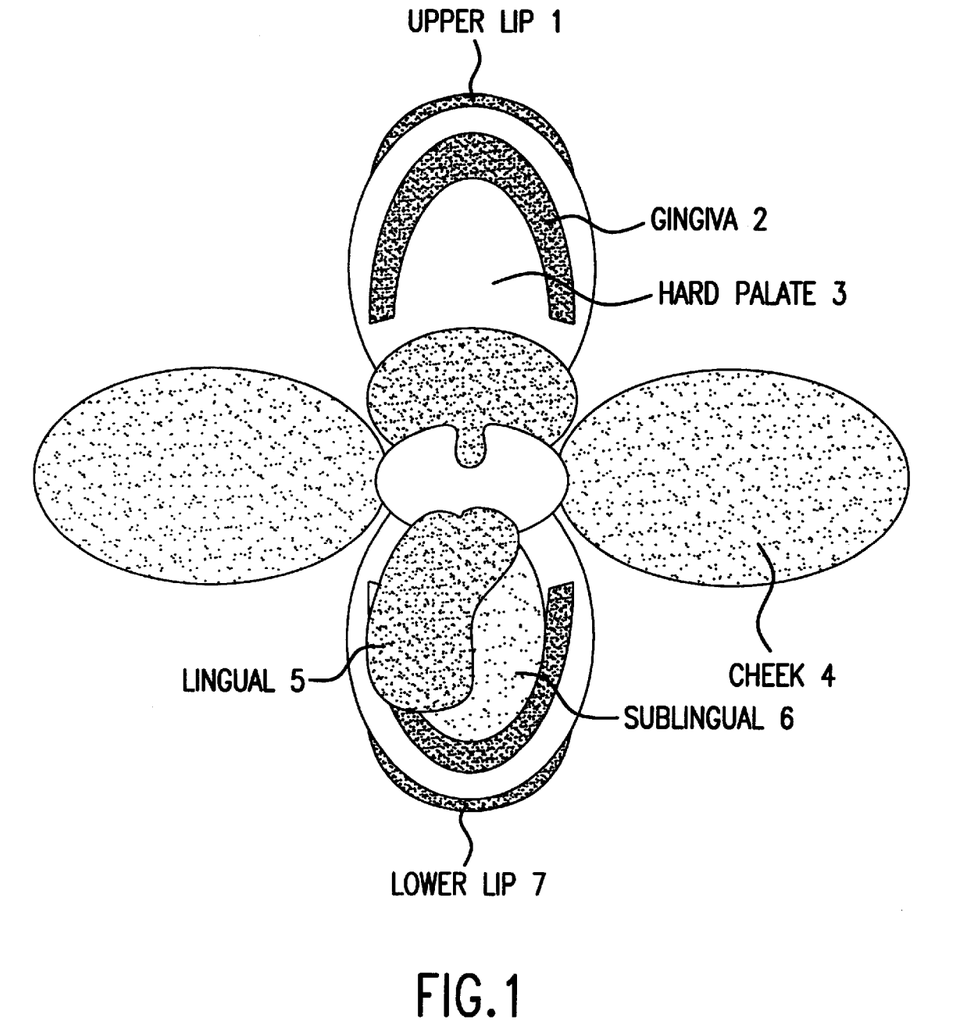
FIG. 1 shows possible application sites in the oral cavity for the inventive dosage unit. (1) is the upper lip; (2) is the gingiva; (3) is the hard palate; (4) is the cheek; (5) is the lingual; (6) is the sublingual; (7) is the lower lip.

Embodiments of the present invention include a process, composition and method of use for a quick dissolving film for local and systemic delivery of pharmaceutical agents to a mucosal surface in a subject. In the following text, specific reference may be made to the oral cavity by way of example. However, it is not intended to limit the scope of the invention to the oral cavity. The dosage unit of the invention may be applied to any mucosal surface as deemed appropriate for the systemic or local delivery of an active agent including vaginal, rectal, and ocular surfaces. For purposes of oral delivery, the films may be applied on lingual, sub-lingual, buccal, gingival, and palatal surfaces (FIG. 1).

For vaginal delivery of such agents as contraceptive agents including nonoxynol or anti-infectives including anti-fungal agents, antibacterial agents and anti-viral agents, or fragrant or hygiene agents; the film should be non-sticky when removed from the packaging but should have mucoadhesive properties when applied in the vagina. Although films containing active agents for use in the vagina have been used, they appear to have some significant drawbacks most particularly the lack of adhesive properties at the mucosal surface. This makes these films impractical to administer. (U.S. Pat. Nos. 5,380,529; 5,595,980 and 5,529,782).

Embodiments of the invention provide improved dosage forms to deliver active agents that are appropriate for all age groups and that physician, parents, patients and family members can administer easily. These dosage forms are economical to prepare and have an extended shelf life. They are easy to handle and non-tacky before administration so as to avoid disintegration prior to use and are conveniently packaged for shelf life, ease of storage and distribution. The dosage form may be administered to the subject by placing the film on a mucous surface, at which time the film becomes a mucoadhesive coating, characterized by the property that it can no longer exist in an independent form and is subsequently dispersed in solution.

Embodiments of the invention provide a delivery system for active agents and other active agents that will dissolve and completely release their contents on a moist mucosal surface—for example in the oral cavity. The release of the active agent occurs without mastication or the need for intake of water. With particular reference to the oral cavity, an embodiment of the invention provides active agents that remain in the oral cavity for treatment or modification of the oral environment; for example, for periodontal disease treatment or breath-odor control. Furthermore, embodiments of the invention further provide improvements that include: improved organoleptic properties (smell and taste), and texture and feel of dosage forms intended to be placed in the oral cavity; a dosage form which "melts" in the mouth and leaves a smooth pleasant after feel following dissolution; and a prolonged retention of the active agent in the mouth following dissolution of the quick dissolving dosage form to extend the residence time of the active agent cleared from the mouth by the production of saliva and subsequent swallowing. Depending on the optimal program for a specific application of the invention, the disintegration time and the dissolution time can be controlled within a prescribed range by adjustment of the formulation and the thickness of the film. In some cases, it is desirable for release of the active agent to occur after dissolution of the film. For these applications, the active agent may be encapsulated in a material with dissolution properties that are different from those of the hydrocolloid. Encapsulation of the active agent also may be utilized to achieve masking of taste for active agents that are bitter. In some cases, two or more different active agents may be included in the film. An example where multiple active agents frequently are administered is cold medications, which often contain several active agents.

"Coating solution" is defined here and in the claims as a viscous and homogeneous mixture of hydrocolloids, active agents and other additives in a solvent. The coating solution is treated according to the method of the invention to form a film.

"Subject" is defined here and in the claims as a human or animal species.

"Thickness" is defined here and in the claims by measurements in mil (a mil=one thousandth of an inch) determined when a film is placed between two microscopic slides.

"Permeation enhancer" as defined here and in the claims is a natural or synthetic molecule which facilitates the absorption of an active agent through a mucosal surface.

"Enzyme inhibitor" as defined here and in the claims is a natural or synthetic molecule which inhibits enzymatic metabolism of an active agent in the saliva or in a mucosal tissue.

"Water Content" is defined here and in the claims as % residual water content per unit dose as measured according to the Karl Fisher method and expressed as percent of the dry weight of the film.

"The hydration rate" is defined here and in the claims as the speed of absorbing water at 25° C. and 75% relative humidity in 24 hours.

"Percentage of swelling" is defined here as a percentage of the initial volume that is increased before dissolving. In an embodiment of the invention, the percentage of swelling is less than 10% in 60 seconds.

Taste modifying agents include flavoring agents, sweetening agents and taste masking agents and are exemplified by: the essential oils or water soluble extracts of menthol, wintergreen, peppermint, sweet mint, spearmint, vanillin, cherry, chocolate, cinnamon, clove, lemon, orange, raspberry, rose, spice, violet, herbal, fruit, strawberry, grape, pineapple, peach, kiwi, papaya, mango, coconut, apple, coffee, plum, watermelon, nuts, durean, green tea, grapefruit, banana, butter, camomile, sugar, dextrose, lactose, mannitol, sucrose, xylitol, malitol, acesulfame potassium, talin, glycyrrhizin, sucralose, aspartame, saccharin, sodium saccharin, sodium cyclamate and honey.

Emulsifying agents include solubilizers and wetting agents and are exemplified by polyvinyl alcohol, sorbitan esters, cyclodextrins, benzyl benzoate, glyceryl monostearate, polyoxyethylene alkyl ethers, polyoxyethylene stearates, poloxamer, polyoxyethylene castor oil derivatives, hydrogenated vegetable oils, bile salts, polysorbates and ethanol. Plasticizers may include glycerin, sorbitol, propylene glycol, polyethylene glycol, triacetin, triethyl citrate (TEC), acetyl triethyl citrate (ATEC) and other citrate esters.

Active agents (for human and veterinary applications) include therapeutic agents, nutritional supplements and hygiene aids. The therapeutic agents are exemplified by analgesics, a-adrenergic receptor blockers, anti-Alzheimer's disease medication, antianginal, antianxiety, antiarrythmics, antiarthritics, antibiotics, anticoagulants/thrombolytics, anticonvulsants/anti-Parkinson medication, antidepressants, anti-diabetics, anti-diarrheal, anti-epileptics, anti-fungal, anti-gout, anti-heartworm medication for dogs, anti-histamines, anti-hypertensives, anti-inflammatories, anti-infectives, antimigraines, anti-nasuants/anti-emetics, anti-neoplastics/anti-tumor active agents, anti-pruitics, anti-psychotics, anti-pyretics, anti-spasmodics, anti-virals, bronchial dilators/anti-asthmatics, calcium antagonists, cardiac agents, cardiotonics, central nervous system actives, contraceptives, coronary vasodilators, cough/cold remedies, dietary supplements, including vitamins and minerals, diuretics, fertility active agents, flea control agents for animals (Ivermectin), $H_2$ receptor antagonists, herbal actives, hormones, hypoglycemics, hypolipidemics, muscle relaxants, ovulation stimulators, peptide active agents, polypeptide active agents, proteins such as insulin, calcitonin, LHRH and the like. Sedatives and hypnotics, sexual dysfunction active agents, sleep aids, smoking cessation aids, steroids and steroidals, tranquilizers, laxatives, ophthalmic preparations, nutritional supplements, breath fresheners, breath deodorants, saliva substitutes, antigingivitis agents, anti-cavity agents, anti-plaque agents, diagnostic indicators, and local anesthetics. Also included are active agents for treatment of osteoporosis, hormone replacement, treatment of periodontal disease, antiseptics, corticosteroids, non steroidal anti-inflammatory agents, antiviral agents and vaccines.

Water soluble inert fillers include mannitol, xylitol, sucrose, lactose, maltodextrin, dextran, dextrin, modified starches, dextrose, sorbitol, and dextrates. The water soluble inert fillers may be used in embodiments of the invention as inert carriers to form a high water soluble dispersion with active agents.

Buffering agents include acidulants and alkalizing agents exemplified by citric acid, fumaric acid, lactic acid, tartaric acid, malic acid, as well as sodium citrate, sodium bicarbonate and carbonate, sodium or potassium phosphate and magnesium oxide.

Coloring agents may include FD & C coloring agents, natural coloring agents, and natural juice concentrates, pigments such as titanium oxide, silicon dioxide and zinc oxide.

Stabilizers as used here and in the claims, include antioxidants, chelating agents, and enzyme inhibitors as exemplified by ascorbic acid, vitamin E, butylated hyroxyanisole (BHA), butylated hydroxytoluene (BHT), propyl gallate, dilauryl thiodipropionate, thiodipropionic acid, gum guaiac, citric acid, edetic acid and its salts and glutathione.

Preservatives which here include anti-microbial agents and non-organic compounds are exemplified by sodium benzoate, parabens and derivatives, sorbic acid and its salts, propionic acids and its salts, sulfur dioxide and sulfites, acetic acid and acetates, nitrites and nitrates.

The mechanical properties of the film is determined by tensile strength modulus, percent elongation (ASTM D882, standard test method for tensile properties of thin plastic sheet) and tear propagation resistance (ASTM D1938, standard test method for tear propagation resistance of plastic film and thin sheet by single tear method). The mechanical properties are measured here using standard protocols as described in Annual Book of ASTM Standards, American National Standards Institute, NY 1995.

The "tensile strength" (psi) is the property of film that requires a load to cause load deformation failure of film.

The "% elongation" is measured when the film snaps as sufficient force is applied so as to exceed the elastic limit.

The "release study" is the percentage of active agents released from the film as a function of time in a suitable dissolution vessel and medium under specified conditions of temperature and pH.

"Dry tack" is quantitative values for tackiness (grams) of dry film by Texture Analyzers (Model TA.XT2i with 6 mm diameter stainless steel cylinder probe) from Texture Technologies Corp. The tackiness after the addition of 10 ml of water on the same surface area is defined as the wet tack (gram) to simulate the adhesion of film upon the contact with a moist mucosal surface. In an embodiment of the invention, the dry tack ranges from 0.2–3.5 grams, with a preferred range of 0.4–2.0 grams and the wet tack is in the range of 35–150 grams with a preferred range of 40–100 grams.

"Tear propagation resistance" is defined here and in the claims as the average force (N) necessary to propagate a tear across a film or sheet under a specified rate of extension as defined in ASTM D1938 and is interpreted from the load time chart. In a preferred embodiment of the invention, the tear resistance ranges from 0.001N–1N with a preferred range of 0.01–1N.

"Disintegration time" is defined here and in the claims as the time (second) at which a film breaks when brought into contact with water or saliva. In an embodiment of the invention, the disintegration time ranges from 1–300 seconds.

"Dissolving time" is defined here and in the claims as the time (seconds or minutes) at which not less than 80% of the tested film is dissolved in an aqueous media or saliva. In an embodiment of the invention, the dissolution time ranges from 10–600 seconds.

"Modulus" is a measurement of stiffness of a film.

A factor that plays a significant role in determining the properties of mucosal surface-coat-forming composition is the viscosity of the hydrocolloid. The viscosity of the hydrocolloid depends on its molecular size, derivation, hydrophobicity and hydrophilicity and the presence of other additives in the formulation. A comparison of films formed from the hydrocolloid, hydroxymethylcellulose, having different viscosity values is shown in Table 9a and 9b.

In embodiments of the invention, a hydrocolloid concentration in the range of 5–99% of the dry weight of the films is provided, more particularly greater than 10%. These films have dry tack and wet tack properties that improve ease of handling and use. The low dry tack properties of the film provide for a physically attractive and easily handled film that is neither fragile nor sticky and can be easily removed from packaging and placed on a mucosal surface. The wet tack properties of the film provide the advantage of stickiness of the moistened film such that when the film is placed on the mucosa, it remains attached at that site until it dissolves. In contrast, if the wet tack is too low, the film can move in the mouth and may be swallowed before dissolving and possibly give rise to choking. Furthermore, the low moisture content and low dry tack of the film enhances the shelf-life of the film and the flexibility of the dosage forms. These properties render the films suitable for easy making, packaging, handling and application.

In an embodiment of the invention, a water soluble polymer (2% polymer solution) is selected having a gelation temperature greater than 70° C. The hydration rate of a hydrocolloid having these features is rapid with a percentage moisture absorption of polymers in the range of 5–20% at 75% humidity at room temperature. The hydration rate is selected according to the desired wettability of the film thereby obviating the need for surfactants. The wet tack of the hydrated film ranges from 35–150 grams more particularly 40–100 grams. The percentage swelling may be less than 10% within 60 seconds. The film is cast so as to have a thickness of 1–20 mil. The water content of the film ranges from 0.5–10% with a preferred range of 1–5%. In embodiments of the invention, the film may be formed using a mixture of two or more types of the same hydrocolloid that differ only in molecular weights and/or different degrees of substitution. The time of dissolution of the film is in the range of 10–600 seconds, (see FIG. 4), the time of disintegration of the film may be 1–300 seconds. The active agent in the film may be encapsulated in a polymer having different chemical or physical properties from the hydrocolloid of the film and having dissolution properties different from those of the hydrocolloid. Examples of the films formed according to the invention having properties that fall into the above ranges are provided in Table 1,3,6 and 7.

The ease of handling is characterized by the dry tack of the film and the flexibility is reflected by the tensile strength, modulus, % elongation and tear resistance of the film. For example, the dry tack is in the range of 0.2–3.5 grams more particularly 0.4–2.0 grams. The tensile strength may be in the range of 1500–10,000 psi, more particularly 2000–8000, more particularly greater than 2000 psi, the modulus is in the range of 35,000–300,000 and the % elongation is less than 20% more particularly 1–10% for a film having a thickness of 2 mil. In embodiments of the invention, the hydrocolloid may be a water soluble non-gelling (at room temperature) natural polysaccharide or derivatives including pectin and derivatives, guar gum arabic, tragacanth gum, xanthan gum, gellan sodium salt, propyleneglycol alginate, starches (amylose, amylopectin), modified starches, hydroxyethyl starch, pullulan, carboxymethyl starch, gum ghatti, okra gum, karaya gum, dextrans, dextrins and maltodextrins, konjac, acemannan from aloe, locust bean gum, tara gum, quince seed gum, fenugreek seed gum, scleroglucan, gum arabic, psyllium seed gum, tamarind gum, oat gum, quince seed gum, carrageenans, scleraglucan, succinoglucan, larch arabinogalactan, flaxseed gum, chondroitin sulfates, hyaluronic acid, curdlan, chitosan, deacetylated konjac, and rhizobium gum.

In embodiments of the invention, the hydrocolloid may be a water soluble non-gelling polypeptide or protein exemplified by gelatins, albumins, milk proteins, soy protein, and whey proteins. The hydrocolloid may further be selected from a group of synthetic hydrocolloids exemplified by any of the following: polyethylene-imine, hydroxyethyl cellulose, sodium carboxymethyl cellulose, carboxymethyl cellulose, hydroxypropyl cellulose, hydroxypropyl methyl cellulose, methyl cellulose, ethyl cellulose, polyacrylic acids, low molecular weight polyacrylamides and their sodium salts (carbomers), polyvinylpyrollidone, polyethylene glycols, polyethylene oxides, polyvinyl alcohols, pluronics, tetronics, and other block co-polymers, carboxyvinyl polymers, and colloidal silicon dioxide. A preferred embodiment of the invention utilizes a hydroxypropyl methyl cellulose having a methoxy content of about 19–30% and hydroxypropyl content of 7–12% and a molecular weight of approximately 50,000–250,000 daltons (Table 9).

In addition to hydrocolloids and the active agents, the films may contain any or all of the following ingredients: emulsifying agents, solubilizing agents, wetting agents, taste modifying agents, plasticizers, active agents, water soluble inert fillers, preservatives, buffering agents, coloring agents, and stabilizers. In a preferred embodiment, the percentage dry weight concentration of at least single ingredients incorporated in a film in each of the following categories is as follows: emulsifying agent (0.1%–0%), plasticizer (0.5–20%), active agents (0.01–75%), taste modifying agents (0.1–10%), coloring agents (0.01–5%), water soluble inert fillers (0.5–50%), preservatives (0.01–10%), buffering agents (0.1–10%) and stabilizers (0.01–5%).

Figure 2:
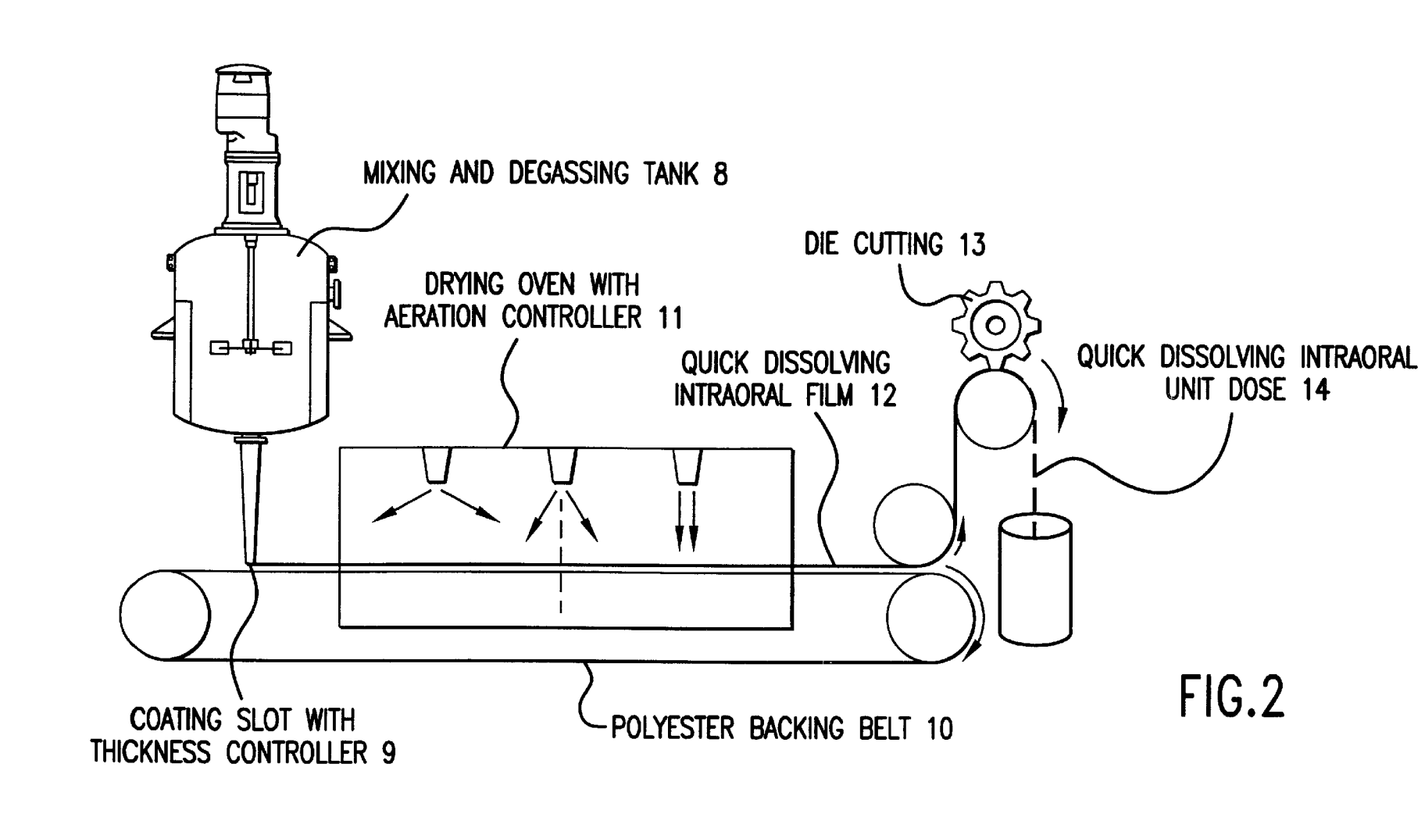
FIG. 2 illustrates one manufacturing process for the dosage unit. (8) is the mixing and degassing tank; (9) is the coating slot with thickness controller; (10) is the polyester backing belt; (11) is the drying oven with aeration controller; (12) is the intraoral film; (13) is the die cutting and (14) is the intraoral unit dose.

Methods for manufacturing the dosage unit of the invention include the solvent casting methods as shown in FIG. 2 or alternatively extrusion methods as exemplified in Example 11. The extrusion method involves blending ingredients to form a film using mechanical force and moderate heat. Significantly, the above processes do not rely on a freeze drying step. Nor do the above processes rely on extremes of heat or cold during manufacture.

Figure 3:
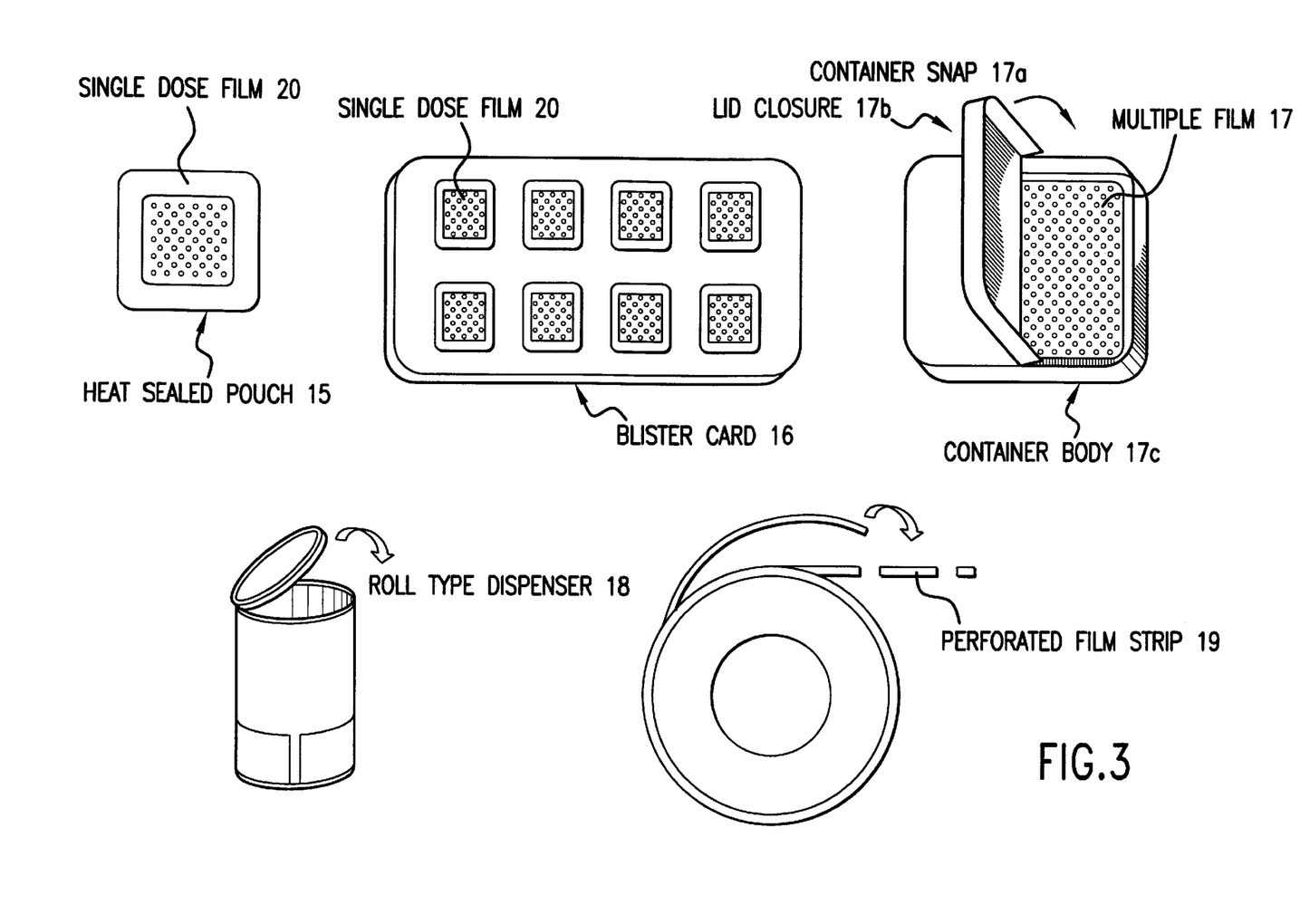
FIG. 3 shows examples of packaging and dispensing devices for the intraoral delivery system. (15) is a heat sealed single pouch; (16) is a multi-unit blister card; (17) is a multi-unit dispensing pack, 17(a) the container snap and 17(b) the lid closure; (18) is a multi-unit roll-type dispenser cylinder; (19) is a perforated film strip; and (20) is a single dose film.

In an embodiment of the invention, the solvent casting method includes a natural or synthetic hydrocolloid that is completely dissolved or dispersed in water or in a water alcoholic solution under mixing to form a homogenous formulation. In addition to the active agent and the hydrocolloid, any of the ingredients listed above may be added and dispersed or dissolved uniformly in the hydrocolloid solution. The active ingredients and flavoring agents can be incorporated before or after film forming. This homogeneous mixture (coating solution) with a solid content of 5–50% and a viscosity of 500–15000 cps was degassed (8) and coated on the non-siliconized side of a polyester film (10) at 5–50 mil wet film thickness (9), more preferably 5–20 mil wet film thickness and dried under aeration at a temperature between 40–100° C. so as to avoid destabilizing the agents contained within the formulation (11). The manufacturing process for forming the dosage unit is illustrated in FIG. 2. The dry film formed by this process is a glossy, stand alone, self supporting, non-tacky and flexible film (12). The dry film is then cut into a suitable shape (13) and surface area for active agent delivery at the preferred site. For example, the cast film can be die-cut into different shapes and sizes using a rotary die. The film may be cut into a size that contains for example, a single dosage unit. For example, a dosage unit may include a film size with surface area of 5 cm$^2$ that contains a dosage of active agent in the range of 20–250 mg (14). The size of the film may be varied according to the dosage required. The dosage contained in each square centimeter is selected according to the active agent. Films are then packaged into a single pouch package, multi-unit blister card or multiple unit dispensers (FIG. 3).

In contrast to the above method, the dry extrusion method does not rely on placing the hydrocolloid in a solvent. Instead, the ingredients of the dosage unit are mixed together in dry form and heated. The heated blend is then forced through an extrusion die to form a film of selected thickness. The film can then be cut and packaged.

The dry extrusion method has a number of advantages. First, it is an economical process. Second, because there is no drying oven, extrusion of the film is faster than solvent coating. Third, the dry extrusion avoids the step of removing residual solvent. Some residual solvent is generally present in the solvent coating process and can affect the safety or stability of the film. Where a film requires an organic solvent rather than water, removal of the solvent from the film may be required by environmental regulations. The extrusion process avoids any need for recovering solvent and avoids residual solvent in the film.

Figure 4:
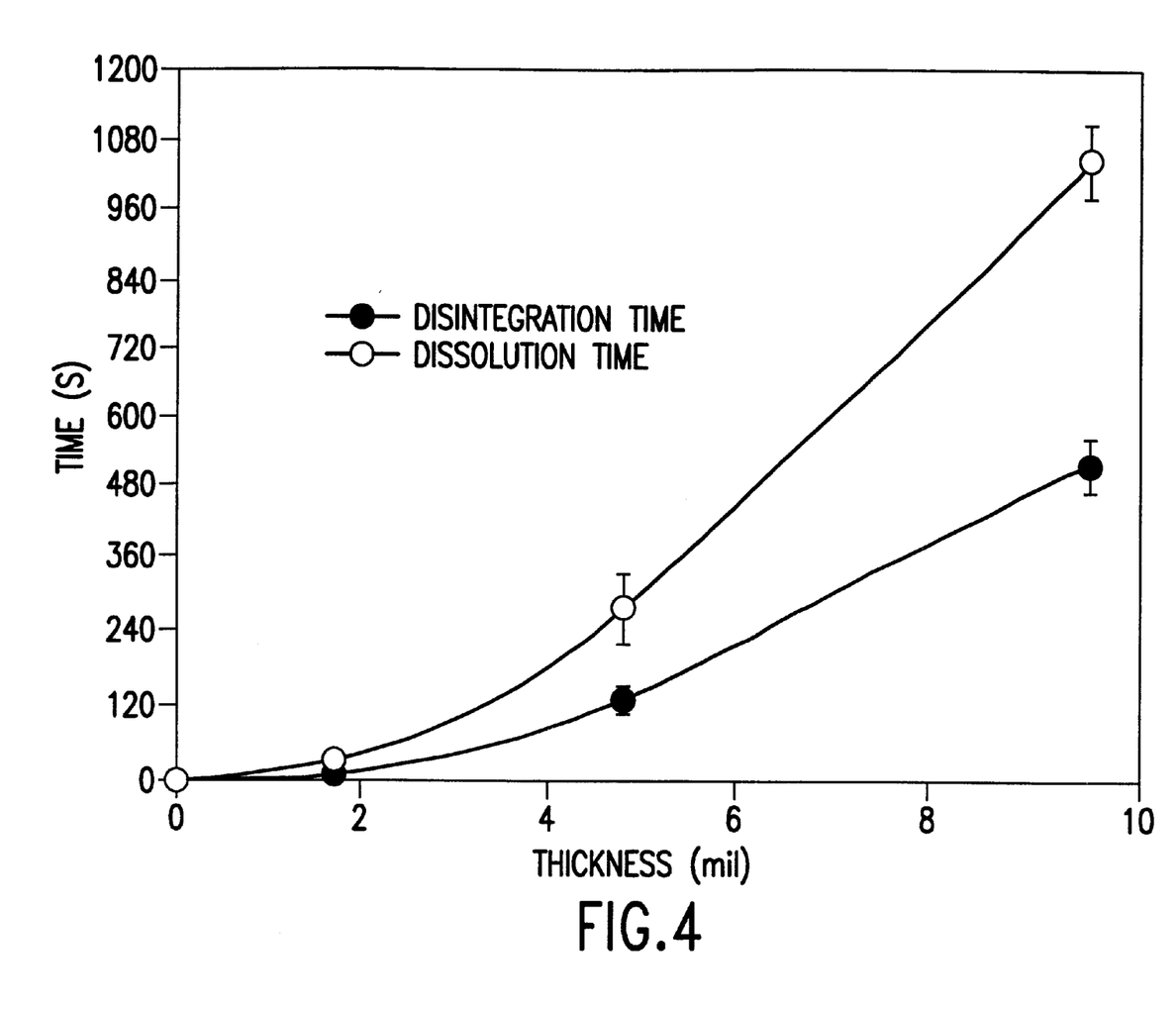
FIG. 4 demonstrates the disintegration and dissolution time of the intraoral delivery system as a function of thickness. --●-- is disintegration time and --○-- is dissolving time.
Figure 5:
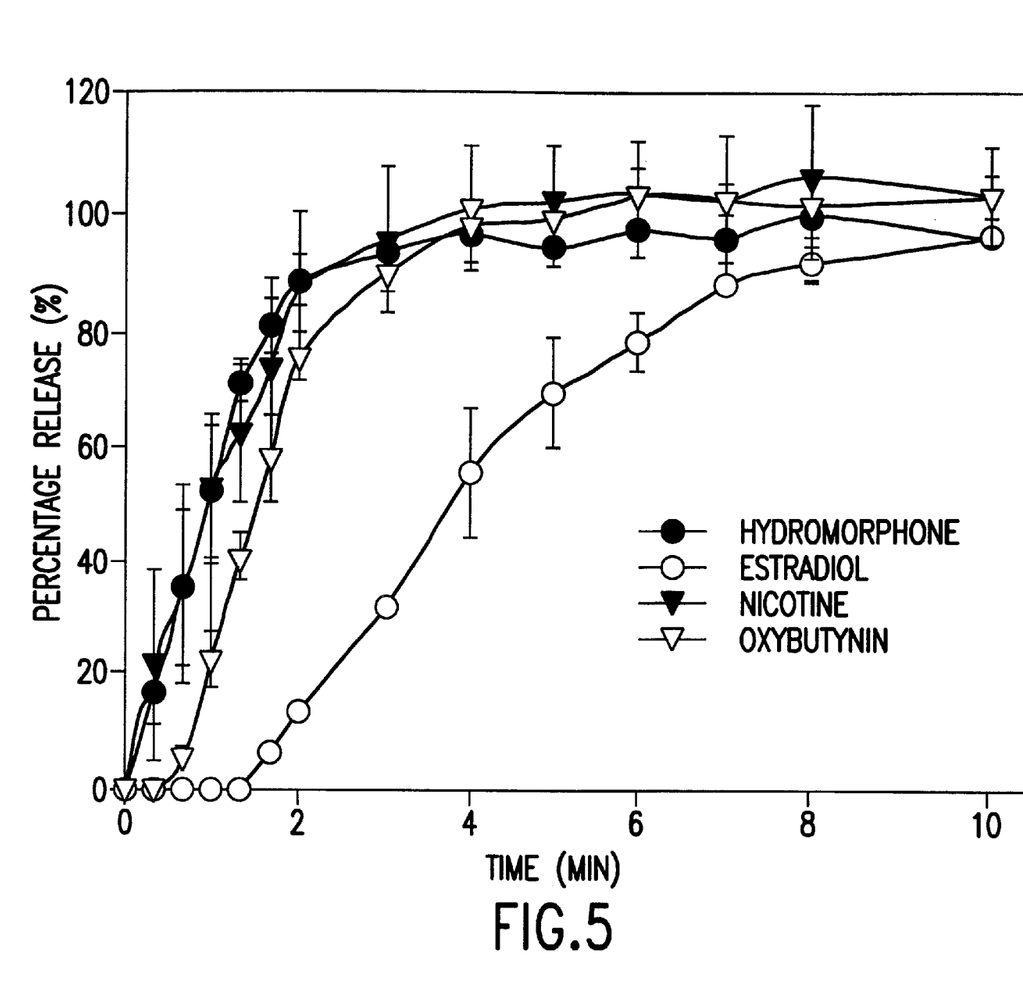
FIG. 5 shows the release profiles of --▼-- nicotine, --▽-- oxybutynin, --●-- hydromorphone and --○-- estradiol.

The dosage unit may be prepared for use by selecting a film that is capable of delivering an effective dose and administering the film to the patient by placing it on a mucosal surface such as the oral mucosa (FIG. 1) where it dissolves in the body fluid for example, saliva (0.5–10 minutes) and is swallowed in liquid form. FIG. 4 graphically represents the rate of disintegration and dissolution for different thickness films. FIG. 5 shows the release profile of four active agents from films according to Examples 5–8. The fraction of the dose absorbed through the mucosal tissue can be facilitated by the use of a permeation enhancer into the film.

The overall bioavailability of the active agent which is absorbed both locally at the mucous membrane and systemically within the gastrointestinal system is improved compared to the same dose of the active agent given in a conventional oral tablet or capsule dosage form. This is exemplified in FIG. 6 and Table 11 which show the improved bioavailability of Sildenafil film over Viagra. The oral retention characteristics, mouth feel properties, flavor and taste of the film can be modified based on the hydrocolloid and other excipients used to prepare the films and the medications.

The invention is illustrated but not meant to be limited to the examples provided below. According to Examples 1–8, the hydrocolloid was dissolved in water under agitated mixing to form a uniform and viscous solution. Additional ingredients were then added sequentially to the viscous solution such as peppermint, aspartame, propyl glycol, benzoic acid and citric acid under agitated mixing until they were uniformly dispersed or dissolved in the hydrocolloid. The resultant mixture was degassed in a vacuum chamber until trapped air bubbles were removed. The viscosity, pH and specific gravity were measured. The formulation was then coated on the non-siliconized side of a polyester film at a wet thickness of 10 mil and dried in a hot air circulating oven at 50° C. for 9 minutes. A glossy, substantially transparent, stand alone, self-supporting, non-tacky and flexible film was obtained after drying. The dry film was cut into different shapes for measurement of dry tack, wet tack, tensile strength modulus, elongation, tear resistance, residual water content, disintegration and dissolution. The dosage form was 25–250 mg in various shapes, sizes, and thickness. Example 9 shows how the properties of dosage units vary when different hydroxymethylcellulose polymers are utilized. Example 10 shows how mucoadhesion can be increased up to at least 84% using an enhancer exemplified by starch graft copolymer. In vivo studies of the dosage unit show that it is well tolerated by patients (Example 12) and shows enhanced bioavailability (Example 13).

EXAMPLES

Examples 1–3

Quick Dissolving Films, Compositions and Associated Properties

The films were prepared as follows: a homogeneous mixture of ingredients was prepared in a coating solution in the amounts indicated in Table 1. The amounts are given as percentage weight of coating solution. The mixture was degassed in a vacuum chamber and coated on the non-siliconized side of a polyester film and dried in a hot air circulating oven to form a self supporting non-tacky and flexible film. The film was then cut into dosage units ready for packaging.

TABLE 1

Formulation of quick dissolving films using several different hydrocolloids.

| Composition: coating solution % | Ex. 1 | Ex. 2 | Ex. 3 |
|---|---|---|---|
| Pullalan (P-20) w % | | 17.5 | |
| Methocel E5 w % | 21.06 | | |
| POLYOX WSR N-10 w % | | | 1.8 |
| PVA (Vinol 125) w % | | 1.5 | |
| Cellulose gum w % | | | 8.1 |
| Propylene glycol w % | 1.0 | | 2.5 |
| Aspartame w % | 0.8 | 0.475 | 0.46 |
| Peppermint w % | 1.0 | 1.0 | 0.6 |
| Citric acid w % | 0.7 | 0.8 | |
| Cremphor EL40 w % | 1.0 | 1.0 | |
| Benzoic acid w % | 0.013 | 0.1 | 0.01 |
| FD&C blue #1 w % | qs. | | |
| FD&C yellow #5 w % | qs. | | |
| Ethanol w % | | 10.6 | |
| Water w % | 74.42 | 67.025 | 85.6 |

TABLE 2

Properties of the film formed from the coating solution of Table 1.

| Properties of dry film | Ex. 1 | Ex. 2 | Ex. 3 |
|---|---|---|---|
| Thickness (mil) | 2.1 | 2.5 | 2.6 |
| Water content % | 1.7 | 8.5 | 8.0 |
| Dry tack (g) | 0.67 | 0.55 | 0.60 |
| Wet tack (g) | 60.16 | 86.64 | 72.27 |
| Tensile strength (psi) | 5242 | 2381 | 2036 |
| % Elongation (sec) | 2.9 | 4 | 2.9 |
| Modulus (psi) | 266834 | 272502 | 44566 |
| Tear resistance (N) | 0.02 | 0.16 | 0.01 |
| Disintegration (sec) | 12 | 20 | 12 |
| Dissolving time (sec) | 41 | 60 | 39 |

TABLE 3

Dry weight percentages for components of Example 1 according to Tables 1 and 2.

| Ingredients | Percentage (w/w) |
|---|---|
| Methocel E5 | 82.35 |
| Propylene glycol | 3.91 |
| Aspartame | 3.13 |
| Citric acid | 2.74 |
| Peppermint oil | 3.91 |
| PEG-40 Hydrogenated castor oil | 3.91 |
| Benzoic acid | 0.5 |
| FD&C blue #1 | qs. |
| FD&C yellow #5 | qs. |

TABLE 4

Mean values for parameters according to Example 1 in Table 1.

| Properties | Value | ±SD (n) |
|---|---|---|
| Weight (g/dosage film) | 0.028 | 0.001 (4) |
| Thickness (mil) | 2.1 | 0.12 (3) |
| PH | 3.07 | (1) |
| Density (g/cm2) | 1.0485 | 0.009 (3) |
| % Water content | 1.7 | 0.24 (2) |
| Dry tack (g) | 0.674 | 0.110 (6) |
| Wet tack (g) | 60.169 | 11.680 (6) |
| Tensile strength (psi) | 5242 | 379 (5) |
| % Elongation | 2.9 | 0.4 (5) |
| Modulus (psi) | 266834 | 7910 (5) |
| Tear-propagation resistance (N) | 0.02 | 0.00 (4) |
| Disintegration time (sec) | 12 | 1 (3) |
| Dissolving time (sec) | 41 | 5 (3) |

Examples 4–8

Hydropropylmethylcellulose Based Quick Dissolving Intraoral Film Containing Therapeutic Agents The films were prepared according to Examples 1–3. Therapeutic agents were added to the homogeneous mixture (coating solution) prior to forming the film.

TABLE 5

| Composition (coating solution) | Ex. 4 | Ex. 5 | Ex. 6 | Ex. 7 | Ex. 8 |
|---|---|---|---|---|---|
| Nicotine | 1.4 | | | | |
| Hydromorphone | | 2.92 | | | |
| Oxybutynin | | | 3.71 | | |
| Estradiol | | | | | 1.49 |
| Peppermint | 1.0 | 1.0 | 1.0 | 1.0 | 1.0 |
| Methocel E5(HPMC) | 21.06 | 21.06 | 2.06 | 21.06 | 21.06 |
| Propylene glycol | 1.0 | 1.0 | 1.01 | 1.0 | 1.0 |
| Aspartame | 0.8 | 0.8 | 0.8 | 0.8 | 0.8 |
| Citric acid | 0.7 | 0.7 | 0.7 | 0.7 | 0.7 |
| Cremphor EL40 | 1.0 | 1.0 | 1.0 | 1.0 | 1.0 |
| Benzoic acid | 0.013 | 0.013 | 0.013 | 0.013 | 0.013 |
| FD&C blue #1 | qs. | | | | |
| FD&C yellow #5 | qs. | | | | |
| Water | 74.43 | 73.03 | 71.51 | 70.72 | 72.94 |

TABLE 6

Properties of the film formed according to the formulation in Table 5

| Properties | Ex. 4 | Ex. 5 | Ex. 6 | Ex. 7 | Ex. 8 |
|---|---|---|---|---|---|
| Thickness (mil) | 3.0 | 2.9 | 2.9 | 3.2 | 2.7 |
| Density (g/cm$^3$) | 1.18 | 1.19 | 1.13 | 1.20 | 1.16 |
| Water content % | 1.8 | 2.93 | 2.42 | 2.32 | 2.31 |
| Dry tack (g) | 0.67 | 0.608 | 0.619 | 1.215 | 0.671 |
| Wet tack (g) | 49.08 | 54.81 | 84.34 | 88.85 | 39.91 |
| Tensile strength (psi) | 4393 | 3373 | 4138 | 3549 | 3688 |
| % Elongation (sec) | 8.3 | 8.3 | 7.6 | 8.1 | 7.5 |
| Modulus (psi) | 45969 | 48168 | 42110 | 41745 | 53334 |
| Tear resistance (N) | 0.03 | 0.02 | 0.01 | 0.03 | 0.01 |
| Disintegration (sec) | 43.0 | 34.3 | 27.3 | 36.0 | 55.7 |
| Dissolving time (sec) | 73.7 | 64.3 | 58.0 | 65.7 | 111.3 |

TABLE 7

Composition of the Sildenafil film (% wet base)

| Composition | Percentage |
|---|---|
| Sildenafil citrate | 28.93 |
| Xylitol | 3.21 |
| Methocel E15 | 4.59 |
| Propylene Glycol | 3.67 |
| Aspartame | 0.46 |
| Benzoic acid | 0.0045 |
| peppermint oil | 0.46 |
| Sodium EDTA | 0.0045 |
| Polyoxamer L-44 | 2.3 |
| Water | 55 |
| polypro 5000 | 0.92 |

TABLE 8

Properties of the film formed according to the formulation in Table 7

| Properties | Ex. 9 |
|---|---|
| Thickness | 3.2 ± 0.1 |
| Density (g/cm$^3$) | 1.230 |
| Dry tack (g) | 1.21 ± 0.19 |
| Wet tack (g) | 23.79 ± 3.45 |
| Tensile strength (psi) | 421 ± 49 |
| % Elongation | 4.0 ± 0.7 |

TABLE 8-continued

Properties of the film formed according to the formulation in Table 7

| Properties | Ex. 9 |
|---|---|
| Modulus (psi) | 31822 ± 6137 |
| Tear resistence (N) | 0.04 ± 00 |
| Disintegration (sec) | 8.3 ± 1.5 |
| Dissolution (sec) | 23.7 ± 1.5 |

Example 9

A Comparison of Properties of Dosage Units Using Different Hydroxypropylmethylcellulose Polymers The properties of a dosage unit according to the invention may be modified by varying individual components. For example, the dissolution of the film may be prolonged by using hydroxypropylmethylcellulose (HPMC) with higher molecular weight as shown below in Table 9.

TABLE 9a

Properties of selected commercial hydroxypropylmethylcellulose polymers.

| | Methocel Type (Dow Pharmaceuticals) | | | | | | |
|---|---|---|---|---|---|---|---|
| Property | E3 | E5 | K3 | E15 | A15 | E50 | F50 |
| % Methoxyl | 29 | 29 | 22 | 29 | 30 | 29 | 28 |
| % Hydroxypropyl | 8.5 | 8.5 | 8.1 | 8.5 | 0 | 8.5 | 5.0 |
| Viscosity 2% (cps) | 2–4 | 4–6 | 2–4 | 12–18 | 12–18 | 40–60 | 40–60 |

*Each value is the mean S ± D, n = 6

TABLE 9b

Properties of films prepared according to Example 1, using different hydroxypropylmethylcellulose polymers

| Property | E3 | E5 | K3 | E15 | A15 | E50 | F50 |
|---|---|---|---|---|---|---|---|
| Dry tack (g) | 0.61 ± 0.08 | 0.67 ± 0.110 | 0.82 ± 0.12 | 0.66 ± 0.09 | 0.52 ± 0.09 | 0.68 ± 0.14 | 0.52 ± 0.12 |
| Wet tack (g) | 93.4 ± 8.95 | 60.169 ± 11.6 | 60.2 ± 8.77 | 65.4 ± 17.8 | 18.4 ± 3.0 | 79.1 ± 17.1 | 64.1 ± 11.2 |
| Tensile strength (psi) | 1921 ± 442 | 5242 ± 379 | 2043 ± 268 | 4316 ± 384 | 3351 ± 165 | 3725 ± 123 | 3905 ± 590 |
| % Elongation | 4.2 ± 1.2 | 2.9 ± 0.4 | 3.8 ± 0.8 | 16.9 ± 4.3 | 11.1 ± 2.4 | 11.4 ± 2.4 | 15.0 ± 3.4 |
| Modulus (psi) | 44368 ± 864 | 266834 ± 79 | 41737 ± 816 | 46889 ± 416 | 35914 ± 964 | 41651 ± 282 | 43644 ± 942 |
| Tear resistence (N) | 0.040.01± | 0.02 ± 0 | 0.05 ± 0.01 | 0.09 ± 0.03 | 0.12 ± 0.02 | 0.05 ± 0.01 | 0.08 ± 0.01 |
| Disintegration (sec) | 17.0 ± 4.4 | 12 ± 1 | 15.3 ± 1.5 | 21.9 ± 1.6 | 161.0 ± 15.9 | 33.2 ± 5.1 | 24.1 ± 1.3 |
| Dissolution (sec) | 35.7 ± 2.1 | 41 ± 5 | 31.0 ± 1.0 | 51.6 ± 1.3 | >600 | 71.6 ± 3.3 | 62.1 ± 2.8 |

Example 10

Enhancement of Mucoadhesion

The enhancement of mucoadhesion was similarly applicable to films of varying thickness. The following formulations were prepared:

TABLE 10

| Composition/Test results | Example 1 | Example 10a | Example 10b |
|---|---|---|---|
| Composition of example 1 | 100% | 99.9% | 95% |
| Starch graft copolymer* | 0 | 0.1% | 5% |
| Mean Mucoadhesion Measurement (g)** | 17.5 | 26.6 | 32.3 |
| Standard deviation | 7.8 | 4.7 | 4.0 |
| Increase in mucoadhesion % | base value | 52% | 84.6% |

*Starch graft copolymers were prepared by polymerization in water using 1:3 Amioca corn starch:acrylic acid (supplied by NSCC) and are described in further detail in U.S. Pat. No. 4,690,996 and Block and Graft Copolymerization, vol 1, R. J. Ceresa, ed. John Wiley and Sons 1973 both references herein incorporated by reference.
**Mucoadhesion was tested using a tensile instrument (e.g. Texture Analyzer) which measures force of detachment of the invention product from a simulated mucosal tissue material. The mucosal-like material is prepared from a mixture of 3.25% gellan gum and 1.6% mucin in water. The product to be tested was brought into contact with the simulated mucosal surface for 5 seconds and detached. The force of detachment was measured as the value of mucoadhesion in grams force (g or gf). Test conditions used are as follows: speed of application = 3 mm/s, speed of detachment = 2 mm/s, force applied before detachment = 150 g, contact time = 5 s, contact surface = 122.7 $mm^2$ Example 11

Preparation of Film Using Dry Extrusion Techniques 77.8g Polyethylene Oxide (Polyox®WSR N-10) was mixed using mechanical force and additional ingredients were added during the mixing as follows: 5.5 g Estradiol, 3.7 g Peppermint, 3.7 g Propylene Glycol, 3.0 g Aspartame, 2.6 g Citric Acid, 3.7 g Cremphor EL 40 and 0.05 g Benzoic acid. The temperature was maintained at about 70° C.

The blend was allowed to mix at 70° C. until uniform. It was then forced through an extrusion die to form a film 5 mils in thickness. The film was then cut into dosage forms ready for packaging.

Example 12

Human Clinical Acute Irritation Study

An initial clinical irritation study of placebo samples formulated according to Example 1 was conducted. Six HPMC-based films were applied by each of 12 subjects within one hour. The site of application and the oral mucosae were evaluated for any acute irritation prior to each application, immediately after each application, one hour and 24 hours after last application. The following indications: erythema, edema, bullae, maceration and discharge were scored on a scale of 0–4. There was no measurable irritation for any of the sites examined and for any of the indications during each application, or one hour and 24 hours after the last application.

Each subject was asked to assess the mouth feel, product taste, sensation and dissolution time for each application. All twelve subjects did not experience any sensation for any application. All subjects described films gave them very smooth mouth feel and indicated the taste of freshness the film delivered into the oral cavity for each application. All subjects felt the dissolution time of the film was very short (<2 min).

The majority of the subjects stated a preference for the film compared with tablets or capsules. All of the subjects indicated that they preferred the film to solutions or syrups.

Example 13

Human Pharmacokinetics Study Showing Increased Bioavailability of a Active Agent Delivered by an Dosage Unit in the Form of a Film A dissolving film suitable for administration via the oral mucosa and containing the active agent, sildenafil citrate, formulated according to Table 7. The properties of the dosage unit are described in Table 8.

Figure 6:
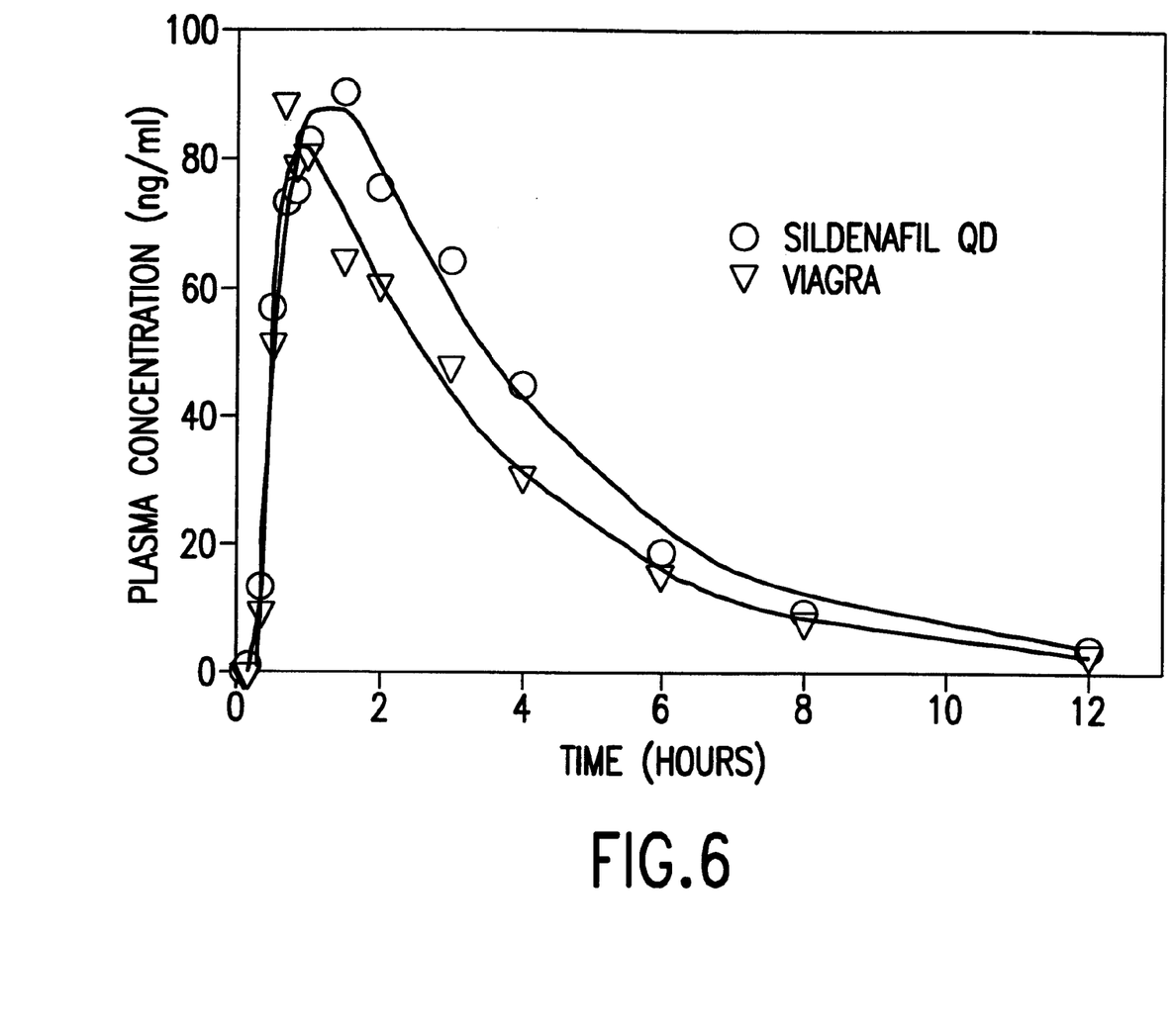
FIG. 6 shows the pharmacokinetics in six subjects after administration of a dissolving film sildenafil formulation and after administration of the commercial tablet containing the same dosage of sildenafil. Sildenafil film --○-- Viagra --▽--.

A two way crossover study was conducted comparing intraoral sildenafil, applied sublingually, with a commercial tablet (Viagra®) at the same dosage. The average plasma levels and the pharmacokinetics analysis are displayed in FIG. 6 and Table 11. FIG. 6 and Table 11 show that the bioavailability of the equivalent dosage from the dissolving film is about 25% higher than the bioavailability of the tablet.

TABLE 11

A comparison of pharmacokinetic parameters of Sildanedil film and Viagra film

| Parameters | Sildanefil (S) film | Viagra (V) film | Ratio S/V | Statistical power |
|---|---|---|---|---|
| AUC* (0–t) | 365.5 | 293.1 | 1.247 | 0.86 |
| AUC (infinity) | 378 | 310.4 | 1.218 | 0.88 |
| Cmax | 109.9 | 106.8 | 1.029 | 0.15 |
| Tmax | 1 | 1 | 1 | 0.08 |
| Ke | 0.354 | 0.285 | 1.245 | 0.32 |
| T | 1.99 | 2.56 | 0.775 | 0.23 |

*Area under the curve

What is claimed is:

1. A dosage unit, comprising: an effective dose of sildenafil citrate; the sildenafil citrate being formed in a solid dispersion with a water soluble inert filler, the solid dispersion being mixed with film forming reagents including a hydropolymer so as to form a film, the film being capable of dissolving on a mucosal surface so as to release the sildenafil citrate; wherein the film exhibits a dry tack value of less than 3.5 g, a wet tack of greater than 35 g, a gelation temperature that is greater than 70° C. for a 2% polymer solution, a dry film thickness of not more than 20 mil, a water content of 0.5 to 10%, a tensile strength greater than 1500 psi, a modulus in the range of 35,000 to 300,000 psi, a % elongation of less than 20%, a tear propagation resistance of 0.001 to 1 N, and a dissolution time of not more than 600 seconds upon application to an oral mucosal surface.

2. A dosage unit comprising a mucosal surface-coat-forming film, wherein the mucosal surface-coat-forming film comprises a water-soluble hydrocolloid, an effective dose of an active agent and a mucosal adhesion enhancer; wherein the active agent is encapsulated within a polymer which is chemically or physically distinct from the hydocolloid; wherein the mucosal adhesion enhancer is a starch graft copolymer; wherein the film exhibits a dry tack value of less than 3.5 g, a wet tack of greater than 35 g, a gelation temperature that is greater than 70° C. for a 2% polymer solution, a dry film thickness of no more than 20 mil, a water content of 0.5 to 10%, a tensile strength greater than 1500 psi, a modulus in the range of 35,000 to 300,000 psi, a % elongation of less than 20%, a tear propagation resistance of 0.001 to 1 N, and a dissolution time of not more than 600 seconds upon application to an oral mucosal surface.

3. The dosage unit of claim 2, wherein the mucosal adhesion enhancer is a copolymer of starch and acrylic acid.

4. The dosage unit of claim 2, wherein the film exhibits a dry tack value of less than 2.0 g.

5. The dosage unit of claim 2, wherein the water-soluble hydrocolloid exhibits a hydration rate in 24 hours of 5–20% at 75% humidity at room temperature.

6. The dosage unit of claim 2, wherein the water-soluble hydrocolloid is a polymer selected from the group consisting of a natural, semi-natural and synthetic biopolymer.

7. The dosage unit of claim 6, wherein the water-soluble hydrocolloid is selected from the group consisting of a polysaccharade and a polypeptide.

8. The dosage unit of claim 6, wherein the water-soluble hydrocolloid comprises a hydroxypropylmethylcellulose polymer.

9. The dosage unit of claim 8, wherein the hydroxypropylmethylcellulose polymer has a molecular weight of less than 200,000 Daltons.

10. The dosage unit of claim 2, wherein the film further comprises at least one of an emulsifier, a plasticizer, a taste modifying agent, a water soluble inert filler, a preservative, a coloring agent, a stabilizer and a buffering agent.

11. The dosage unit of claim 2, wherein the film further comprises an emulsifier present at a concentration in the range of 0.1 to 10 wt % of the dosage unit.

12. The dosage unit of claim 2, wherein the film further comprises a taste modifying agent comprising at least one of a sweetening agent, a flavoring agent and a taste masking agent.

13. The dosage unit of claim 2, wherein the film further comprises a water soluble inert filler present at a concentration in the range of 0.5 to 50 wt % of the dosage unit.

14. The dosage unit of claim 2, wherein the film further comprises a preservative present at a concentration in the range of 0.01 to 10 wt % of the dosage unit.

15. The dosage unit of claim 2, wherein the active agent is present at a concentration in the range of 0.01 to 75 wt % of the dosage unit.

16. The dosage unit of claim 2, wherein the active agent is selected from the group consisting of a therapeutic agent, a dietary supplement and a hygiene aid.

17. The dosage unit of claim 16, wherein the therapeutic agent is sildenafil citrate.

18. The dosage unit of claim 16, wherein the therapeutic agent is selected from the group consisting of nicotine, hydromorphone, oxybutynine and estradiol.

19. The dosage unit of claim 2, wherein the film has a dry film thickness in the range of 1 to 20 mil.

20. The dosage unit of claim 19, wherein the film has a dry film thickness of less than 10 mils.

21. The dosage unit of claim 2, wherein the film exhibits a dissolution time in the range of 10 to 600 seconds upon application to an oral mucosal surface.

22. The dosage unit of claim 2, wherein the film further exhibits a disintegration time in the range of 1 to 300 seconds upon application to an oral mucosal surface.

23. The dosage unit of claim 2, wherein the active agent is encapsulated within a polymer, wherein the polymer is chemically or physically distinct from the hydrocolloid.

24. The dosage unit of claim 2, wherein the dosage unit comprises at least two active agents.

25. The dosage unit of claim 2, wherein the mucosal adhesion enhancer is present at a concentration of up to 50wt %.

26. A dosage unit comprising a mucosal surface-coat-forming film, wherein the mucosal surface-coat-forming film comprises a water soluble hydrocolloid and an effective dose of an active agent, wherein the active agent comprises sildenafil citrate; wherein the mucosal surface-coat-forming film exhibits a dry tack value of less than 3.5 g, a wet tack of greater than 35 g, a gelation temperature that is greater than 70° C. for a 2% polymer solution, a dry film thickness of not more than 20 mil, a water content of 0.5 to 10%, a tensile strength greater than 1500 psi, a modulus in the range of 35,000 to 300,000 psi, a % elongation of less than 20%, a tear propagation resistance of 0.001 to 1 N, and a dissolution time of not more than 600 seconds upon application to an oral mucosal surface.

27. The dosage unit of claim 26, wherein the active agent further comprises xylitol and wherein the xylitol and sildenafil citrate form a solid dispersion.

28. The dosage unit of claim 27, wherein the mass ratio of sildenafil citrate to xylitol is 9/1.

29. The dosage form of claim 27, wherein the dosage unit further comprises a mucosal adhesion enhancer.

30. The dosage unit of claim 29, wherein the mucosal adhesion enhancer is a starch graft copolymer.

31. The dosage unit of claim 29, wherein the mucosal adhesion enhancer is a copolymer of starch and acrylic acid.

32. The dosage unit of claim 27, wherein the film exhibits a dry tack value of less than 2.0 g.

33. The dosage unit of claim 27, wherein the water-soluble hydrocolloid exhibits a gelation temperature that is greater than 70° C. for a 2% polymer solution.

34. The dosage unit of claim 27, wherein the water-soluble hydrocolloid exhibits a hydration rate in 24 hours of 5–20% at 75% humidity at room temperature.

35. The dosage unit of claim 27, wherein the water-soluble hydrocolloid is a polymer selected from the group consisting of a natural, semi-natural and synthetic biopolymer.

36. The dosage unit of claim 35, wherein the water-soluble hydrocolloid is selected from the group consisting of a polysaccharade and a polypeptide.

37. The dosage unit of claim 35, wherein the water-soluble hydrocolloid comprises a hydroxypropylmethylcellulose polymer.

38. The dosage unit of claim 37, wherein the hydroxypropylmethylcellulose polymer has a molecular weight of less than 200,000 Daltons.

39. The dosage unit of claim 27, wherein the film further comprises at least one of an emulsifier, a plasticizer, a taste modifying agent, a water soluble inert filler, a preservative, a coloring agent, a stabilizer and a buffering agent.

40. The dosage unit of claim 27, wherein the film further comprises an emulsifier present at a concentration in the range of 0.1 to 10 wt % of the dosage unit.

41. The dosage unit of claim 27, wherein the film further comprises a taste modifying agent comprising at least one of a sweetening agent, a flavoring agent and a taste masking agent.

42. The dosage unit of claim 27, wherein the film further comprises a water soluble inert filler present at a concentration in the range of 0.5 to 50 wt % of the dosage unit.

43. The dosage unit of claim 27, wherein the film further comprises a preservative present at a concentration in the range of 0.01 to 10 wt % of the dosage unit.

44. The dosage unit of claim 27, wherein the active agent is present at a concentration in the range of 0.01 to 75 wt % of the dosage unit.

45. The dosage unit of claim 27, wherein the film has a dry film thickness in the range of 1 to 20 mil.

46. The dosage unit of claim 45, wherein the film has a dry film thickness of less than 10 mils.

47. The dosage unit of claim 27, wherein the film exhibits a dissolution time in the range of 10 to 600 seconds upon application to an oral mucosal surface.

48. The dosage unit of claim 27, wherein the film further exhibits a disintegration time in the range of 1 to 300 seconds upon application to an oral mucosal surface.

49. The dosage unit of claim 27, wherein the active agent is encapsulated within a polymer, wherein the polymer is chemically or physically distinct from the hydrocolloid.

50. The dosage unit of claim 27, wherein the dosage unit comprises at least two active agents.

51. The dosage unit of claim 27, wherein the mucosal adhesion enhancer is present at a concentration of up to 50 wt %.

* * * * *